US011872011B2

(12) United States Patent
Atkin

(10) Patent No.: US 11,872,011 B2
(45) Date of Patent: *Jan. 16, 2024

(54) PULSE OXIMETER WITH CELLULAR COMMUNICATION CAPABILITY

(71) Applicant: Smart Meter Corporation, Montebello, NY (US)

(72) Inventor: Benjamin Atkin, Miami, FL (US)

(73) Assignee: Smart Meter Corporation, Montebello, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/139,326

(22) Filed: Apr. 25, 2023

(65) Prior Publication Data

US 2023/0255488 A1 Aug. 17, 2023

Related U.S. Application Data

(63) Continuation of application No. 17/517,841, filed on Nov. 3, 2021.

(Continued)

(51) Int. Cl.
*A61B 5/1455* (2006.01)
*A61B 5/00* (2006.01)
*A61B 5/024* (2006.01)

(52) U.S. Cl.
CPC ............ *A61B 5/0022* (2013.01); *A61B 5/024* (2013.01); *A61B 5/14551* (2013.01);
(Continued)

(58) Field of Classification Search
CPC ..... A61B 5/0022; A61B 5/0002; A61B 5/024; A61B 5/1455; A61B 5/14551;
(Continued)

(56) References Cited

U.S. PATENT DOCUMENTS

2005/0085704 A1* 4/2005 Schulz ............... A61B 5/14552
600/344
2006/0220881 A1* 10/2006 Al-Ali .................. A61B 5/0022
600/310

(Continued)

*Primary Examiner* — Chu Chuan Liu
(74) *Attorney, Agent, or Firm* — Bochner PLLC; Andrew D. Bochner

(57) ABSTRACT

A pulse oximeter is described. The pulse oximeter includes at least a sensor component, an engine, a display, and a microphone. The sensor component includes a receiving portion configured to receive a finger of an individual therein, an emitter component configured to emit light at one or more wavelengths into a tissue of the finger of the individual, and a detector component configured to detect the light originating from the emitter component that emanates from the tissue of the finger of the individual after passing through the tissue. The engine is configured to calculate physiological parameters for the individual based on data received from the sensor component. The engine includes a memory housing a first user profile associated with a first user and a second user profile associated with a second user and a processor connected to the memory. The processor includes a voice activation component, which uses algorithms to: analyze the audio input, compare the audio input to commands stored in the memory, determine that the audio input corresponds to a command of the commands stored in the memory based on the comparison, and process and execute the command. The display is configured to display the physiological parameters and other data to the individual.

18 Claims, 7 Drawing Sheets

Related U.S. Application Data

(60) Provisional application No. 63/115,935, filed on Nov. 19, 2020.

(52) U.S. Cl.
CPC ............ *A61B 5/742* (2013.01); *A61B 5/7405* (2013.01); *A61B 5/749* (2013.01)

(58) Field of Classification Search
CPC ... A61B 5/14552; A61B 5/7405; A61B 5/742; A61B 5/749
See application file for complete search history.

(56) References Cited

U.S. PATENT DOCUMENTS

| | | | | |
|---|---|---|---|---|
| 2008/0082339 A1* | 4/2008 | Li | ............................ | G16Z 99/00 |
| | | | | 704/E15.045 |
| 2011/0213225 A1* | 9/2011 | Bernstein | ................ | G16H 40/67 |
| | | | | 600/309 |
| 2014/0244205 A1* | 8/2014 | Van Slyke | .......... | A61B 5/02416 |
| | | | | 702/124 |
| 2015/0223731 A1* | 8/2015 | Sahin | ........................ | A61B 5/16 |
| | | | | 600/595 |

* cited by examiner

--PRIOR ART--

--PRIOR ART--

PULSE OXIMETER WITH CELLULAR COMMUNICATION CAPABILITY

CROSS-REFERENCE TO RELATED APPLICATIONS SECTION

This application is a U.S. Non-Provisional Patent Application that claims priority to U.S. Provisional Patent Application Ser. No. 63/115,935 filed on Nov. 19, 2020, the entire contents of which are hereby incorporated by reference in their entirety.

FIELD OF THE EMBODIMENTS

The field of the invention and its embodiments relate to a pulse oximeter. More specifically, the field of the invention and its embodiments relate to a pulse oximeter that can interact with a mobile device over a network.

BACKGROUND OF THE EMBODIMENTS

Pulse oximetry is a test used to measure the oxygen level (oxygen saturation) of the blood. It is an easy measure of how well oxygen is being sent to parts of one's body, such as the arms and legs. A pulse oximeter may be used to monitor the health of individuals with any type of condition that can affect blood oxygen levels, such as: chronic obstructive pulmonary disease (COPD), asthma, pneumonia, lung cancer, anemia, heart attack or heart failure, and congenital heart defects, among others. However, for some conditions, such as COPD and congestive heart failure, one may need a device that can continuously monitor ones's oxygen saturation.

Review of Related Technology:

U.S. Pat. No. 6,912,413 B2 relates to pulse oximeter devices used to measure blood oxygenation. The current trend towards mobile oximeters has brought the problem of how to minimize power consumption without compromising on the performance of the device. To tackle this problem, this reference provides a method for controlling optical power in a pulse oximeter. The signal-to-noise ratio of the received baseband signal is monitored, and the duty cycle of the driving pulses is controlled in dependence on the monitored signal-to-noise ratio, preferably so that the optical power is minimized within the confines of a predetermined lower threshold set for the signal-to-noise ratio. In this way the optical power is made dependent on the perfusion level of the subject, whereby the power can be controlled to a level which does not exceed that needed for the subject.

U.S. Pat. No. 6,963,767 B2 relates to pulse oximeters used to measure blood oxygenation. The current trend towards lower power consumption has brought a problem of erroneous readings caused by intrachannel crosstalk, i.e. errors due to the coupling of undesired capacitive, inductive, or conductive (resistive) pulse power from the emitting side of the pulse oximeter directly to the detecting side of the oximeter. The pulse oximeter of the reference includes a means for detecting whether intrachannel crosstalk is present and whether it will cause erroneous results in the oxygenation measurements.

U.S. Pat. No. 7,349,726 B2 relates to a system and method for measuring blood oxygen saturation. Specifically, embodiments of the reference include emitting light having a wavelength spectrum that is optimized for an oxygen saturation reading less than 80 percent, detecting the light, and transmitting signals based on the detected light.

U.S. Pat. No. 6,711,425 B1 relates to an improved pulse oximeter (sensor and monitor) that uses a plurality of wavelengths selected to provide sensitivity to both oxygen saturation and deviations in tissue site characteristic(s) from conditions at calibration. The monitor detects and/or removes the effects of deviations on $SpO_2$ calibration, of particular value in fetal/newborn monitoring.

Various pulse oximeter devices and systems exist. However, their means of operation are substantially different from the present disclosure, as the other inventions fail to solve all the problems taught by the present disclosure.

SUMMARY OF THE EMBODIMENTS

The present invention and its embodiments relate to a pulse oximeter. More specifically, the field of the invention and its embodiments relate to a pulse oximeter that can interact with a mobile device over a network.

A first embodiment of the present invention describes a system. The system includes numerous components, such as: a network, a pulse oximeter, and a mobile device. The pulse oximeter includes a sensor component and an engine. The sensor component includes a first side disposed opposite a second side and a receiving portion configured to receive a finger of an individual therein. The first side of the sensor component comprises an emitter component that is configured to emit light at one or more wavelengths into a tissue of the finger of the individual. The second side of the sensor component comprises a detector component that is configured to detect the light originating from the emitter component that emanates from the tissue of the finger of the individual after passing through the tissue.

The engine is connected to the sensor component and is configured to calculate physiological parameters for the individual (e.g., blood oxygen saturation readings and/or pulse rate readings, among others) based on data received from the sensor component. The engine includes numerous components, such as: a memory and a processor connected to the memory and including a voice activation component. The memory is configured to house a first user profile associated with a first user and a second user profile associated with a second user. The first user profile comprises blood oxygen saturation readings for the first user, pulse rate readings for the first user, and/or a unique identifier for the first user, among other information or data. The second user profile comprises blood oxygen saturation readings for the second user, pulse rate readings for the second user, and/or a unique identifier for the second user, among other information or data.

The pulse oximeter also includes a microphone that is configured to receive an audio input from the individual. Further, the voice activation component includes one or more algorithms. The one or more algorithms are configured to: analyze the audio input received via the microphone, compare the audio input to commands stored in the memory, determine that the audio input corresponds to a command of the commands stored in the memory based on the comparison, and process and execute the command. The pulse oximeter may further include a display that shows/displays the physiological parameters and other data to the individual and a data input device configured to receive a physical input from the individual.

The mobile device is configured to interact with the pulse oximeter via the network. In an example, the mobile device comprises an application executable on the mobile device, where the application is configured to track blood oxygen saturation readings and/or pulse rate readings for the first user or the second user.

In some examples, the mobile device is configured to: send a signal via the network to the processor when the mobile device is in proximity to the pulse oximeter. In response to receiving the signal, the processor is configured to: select a user profile from the memory corresponding to an owner of the mobile device, and store a blood oxygen saturation reading and/or a pulse rate reading of the individual in the first user profile if the owner of the mobile device is the first user or store the blood oxygen saturation reading and/or a pulse rate reading in the second user profile if the owner of the mobile device is the second user.

In another example, the system may include a key fob that contains wireless signal capabilities. The key fob is configured to transmit a signal to the processor when the key fob is in proximity of the pulse oximeter. In response to receiving the signal from the key fob, the processor is configured to: select a user profile from the memory corresponding to an owner of the key fob, and store a blood oxygen saturation reading and/or a pulse rate reading of the individual in the first user profile if the owner of the key fob is the first user or store the blood oxygen saturation reading and/or a pulse rate reading in the second user profile if the owner of the key fob is the second user.

A second embodiment of the present invention describes a pulse oximeter. The pulse oximeter includes a sensor component. The sensor component includes a first side disposed opposite a second side and a receiving portion configured to receive a finger of an individual therein. The first side of the sensor component comprises an emitter component configured to emit light at one or more wavelengths into a tissue of the finger of the individual. The second side of the sensor component comprises a detector component configured to detect the light originating from the emitter component that emanates from the tissue of the finger of the individual after passing through the tissue.

The pulse oximeter also includes an engine that is configured to calculate physiological parameters for the individual (e.g., blood oxygen saturation readings and/or pulse rate readings, among others) based on data received from the sensor component. Specifically, the engine includes: a memory and a processor coupled to the memory and including a voice activation component. The memory is configured to house a first user profile associated with a first user and a second user profile associated with a second user. The first user profile comprises blood oxygen saturation readings for the first user, pulse rate readings for the first user, and/or a unique identifier for the first user, among other information/data. The user profile comprises blood oxygen saturation readings for the second user, pulse rate readings for the second user, and/or a unique identifier for the second user, among other information/data.

The pulse oximeter also includes a microphone that is configured to receive an audio input from the individual. Further, the pulse oximeter includes a display that is configured to show/display the physiological parameters and other data to the individual. Further, the voice activation component includes one or more algorithms that are configured to: analyze the audio input received via the microphone, compare the audio input to commands stored in the memory, determine that the audio input corresponds to a command of the commands stored in the memory based on the comparison, and process and execute the command. It should be appreciated that the pulse oximeter may also communicate with a mobile device via a network.

The display may further include one or more indicators configured to encourage use of the pulse oximeter. Such indicators may comprise one or more light-emitting diodes (LEDs). The first user is associated with a first color of light configured to be emitted from the one or more indicators and the second user is associated with a second color of light configured to be emitted from the one or more indicators. The first color of light differs from the second color of light. The first color of light is stored in the first user profile and the second color of light is stored in the second user profile.

Further, the one or more indicators are configured to project or flash the first color of light if the first user fails to use the pulse oximeter for a predetermined period of time. The one or more indicators are configured to project or flash the second color of light if the second user fails to use the pulse oximeter for the predetermined period of time. In other examples, the one or more indicators comprise an audio functionality such that the one or more indicators project or flash light and/or emanate a sound when the individual is within a proximity of the pulse oximeter.

In general, the present invention succeeds in conferring the following benefits and objectives.

The present invention describes a pulse oximeter that can interact with a mobile device over a network.

The present invention describes a pulse oximeter that has multi-user functionality.

The present invention describes a pulse oximeter that has voice activation capabilities.

DESCRIPTION OF THE PREFERRED EMBODIMENTS

Figure 1:
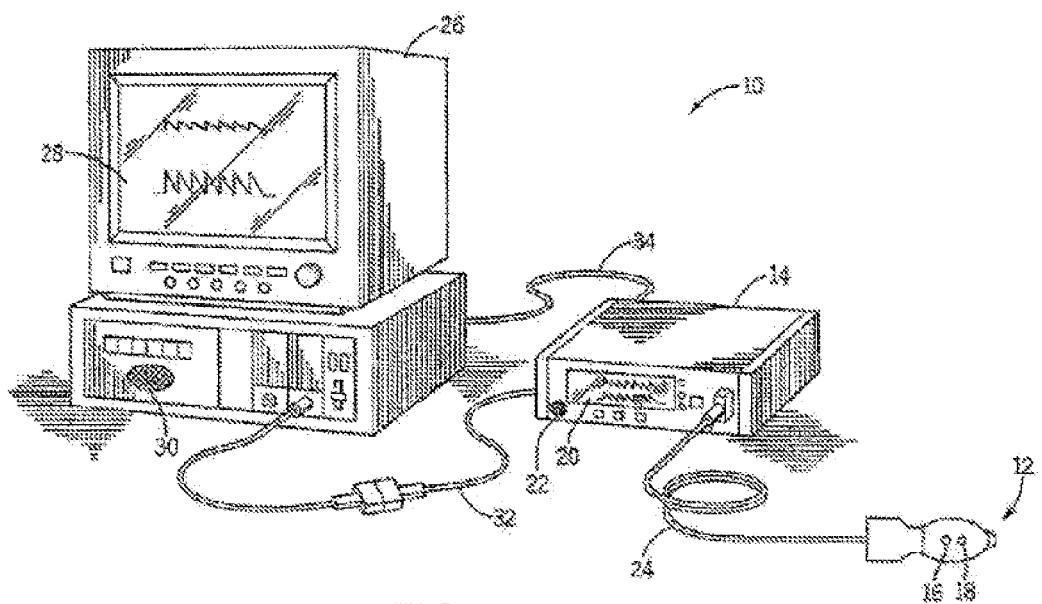
FIG. 1 depicts a schematic diagram of a traditional pulse oximetry system known in the art field, according to at least some embodiments disclosed herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As described herein, pulse oximetry is a non-invasive method for monitoring a person's oxygen saturation. Oxygen saturation is the fraction of oxygen-saturated hemoglobin relative to total hemoglobin in the blood. The human body requires and regulates a precise and specific balance of oxygen in the blood. Normal arterial blood oxygen saturation levels in humans are between 95 percent to 100 percent. If the level is below 90 percent, it is considered low and is called hypoxemia. Arterial blood oxygen levels below 80 percent may compromise organ function, such as the brain and heart, and should be promptly addressed. Continued low oxygen levels may lead to respiratory or cardiac arrest. Oxygen therapy may be used to assist in raising blood oxygen levels.

Pulse oximetry is the current standard of care for the continuous monitoring of arterial oxygen saturation ($SpO_2$). Pulse oximeters provide instantaneous in vivo measurements of arterial oxygenation, and thereby provide early warning of arterial hypoxemia, for example. A typical pulse oximeter comprises a computerized measuring unit and a probe attached to the patient, typically to his or her finger. The probe includes a light source for sending an optical signal through the tissue and a photodetector for receiving the signal after transmission through the tissue. On the basis of the transmitted and received signals, light absorption by the tissue can be determined.

During each cardiac cycle, light absorption by the tissue varies cyclically. During the diastolic phase, absorption is caused by venous blood, tissue, bone, and pigments, whereas during the systolic phase, there is an increase in absorption, which is caused by the influx of arterial blood into the tissue. Pulse oximeters focus the measurement on this arterial blood portion by determining the difference between the peak absorption during the systolic phase and the constant absorption during the diastolic phase. As such, pulse oximetry is based on the assumption that the pulsatile component of the absorption is due to arterial blood only.

Light transmission through an ideal absorbing sample is determined by the Lambert-Beer equation, which includes the following:

$$I_{out}=I_{in}e^{-\varepsilon DC},\qquad\text{[Equation 1]}$$

where $I_{in}$ refers to the light intensity entering the sample,
$I_{out}$ refers to the light intensity received from the sample,
D is the path length through the sample,
$\varepsilon$ is the extinction coefficient of the analyte in the sample at a specific wavelength, and
C is the concentration of the analyte.
When $I_{in}$, D, and $\varepsilon$ are known, and $I_{out}$ is measured, the concentration C can be calculated.

In pulse oximetry, in order to distinguish between the two species of hemoglobin, oxyhemoglobin ($HbO_2$) (or the oxygen-loaded form of hemoglobin) and deoxyhemoglobin (RHb) (or the form of hemoglobin without oxygen), absorption must be measured at two different wavelengths. As such, the probe includes two different light emitting diodes (LEDs). The wavelength values commonly used are 660 nm and 940 nm, since the two species of hemoglobin have substantially different absorption values at these wavelengths. Each LED is illuminated in turn at a frequency which is typically several hundred Hz.

The accuracy of pulse oximeter readings is affected by several factors. First, dyshemoglobins that do not participate in oxygen transport (e.g., methemoglobin (MetHb) and carboxyhemoglobin (CoHb)) absorb light at the wavelengths used in the measurement. As described herein, "MetHb" is a hemoglobin in the form of metalloprotein, in which the iron in the heme group is in the $Fe^{3+}$ state, not the $Fe^{2+}$ of normal hemoglobin. Methemoglobin cannot bind oxygen, which means it cannot carry oxygen to tissues. As described herein, "CoHb" is a stable complex of carbon monoxide and hemoglobin that forms in red blood cells upon contact with carbon monoxide. Pulse oximeters are calibrated to measure oxygen saturation on the assumption that the patient's blood composition is the same as that of a healthy, non-smoking individual. Therefore, if these species of hemoglobin are present in higher concentrations than normal, a pulse oximeter may display erroneous data.

Next, intravenous dyes used for diagnostic purposes may cause considerable deviation in pulse oximeter readings. Further, coatings, such as nail polish, may impair the accuracy of a pulse oximeter. Additionally, the optical signal may be degraded by both noise (such as from the ambient light received by the photodetector) and motion artifacts.

FIG. 1 is a perspective view of an embodiment of a traditional pulse oximetry system 10 known in the art field. The pulse oximetry system 10 of FIG. 1 includes numerous components, such as: a sensor 12 (e.g., a probe) and/or a pulse oximetry monitor 14, among others not explicitly depicted herein. It should be appreciated that the pulse oximetry system 10 may have multiple user functionality and may be beneficial for those individuals needing to consistently track health parameters, such as ones's oxygen saturation.

Moreover, the sensor 12 includes an emitter 16 for emitting light at one or more wavelengths into a patient's tissue. The sensor 12 also includes a detector 18 that detects the light originating from the emitter 16 that emanates from the patient's tissue after passing through the tissue. The emitter 16 and the detector 18 may be on opposite sides of a user's finger, which is received by the sensor 12, in which case the light that is emanating from the tissue has passed completely through the users finger.

The sensor 12 may be connected to and draw power from the monitor 14. Alternatively, the sensor may 12 be wirelessly connected to the monitor 14 and include its own battery or power supply (not shown). The monitor 14 may be configured to calculate physiological parameters based on data received from the sensor 12 relating to light emission and detection.

Further, the monitor 14 includes a display 20 configured to display the physiological parameters and/or other data. In the embodiment shown, the monitor 14 also includes a speaker 22 to provide an audible alarm in the event that the patient's physiological parameters are not within a predetermined range, as defined based on patient characteristics. As depicted, the sensor 12 is communicatively coupled to the monitor 14 via a first cable 24 or other similar means. However, in other embodiments a wireless transmission device (not shown) or the like may be utilized instead of or in addition to the first cable 24.

In the illustrated embodiment of FIG. 1, the pulse oximetry system 10 also includes a multi-parameter patient monitor 26. The multi-parameter patient monitor 26 may be configured to calculate physiological parameters and to provide a central display 28 for information from the monitor 14 and from other medical monitoring devices or systems (not shown). For example, the multiparameter patient monitor 26 may be configured to display a patient's oxygen saturation reading generated by the pulse oximetry monitor 14, pulse rate information from the monitor 14, and a blood pressure reading from a blood pressure monitor (not shown) on the display 28. Additionally, the multi-parameter patient monitor 26 may emit a visible or audible alarm via the display 28 and/or a speaker 30 if the patient's physiological characteristics are found to be outside of the predetermined range defined as "normal."

The monitor 14 may be communicatively coupled to the multi-parameter patient monitor 26 via a second cable 32 or a third cable 34 coupled to a sensor input port or a digital communications port, respectively. In addition, the monitor 14 and/or the multi-parameter patient monitor 26 may be connected to a network to enable the sharing of information with servers or other workstations (not shown). The monitor 14 may be powered by a battery (not shown) or by a power source, such as a wall outlet.

Figure 2:
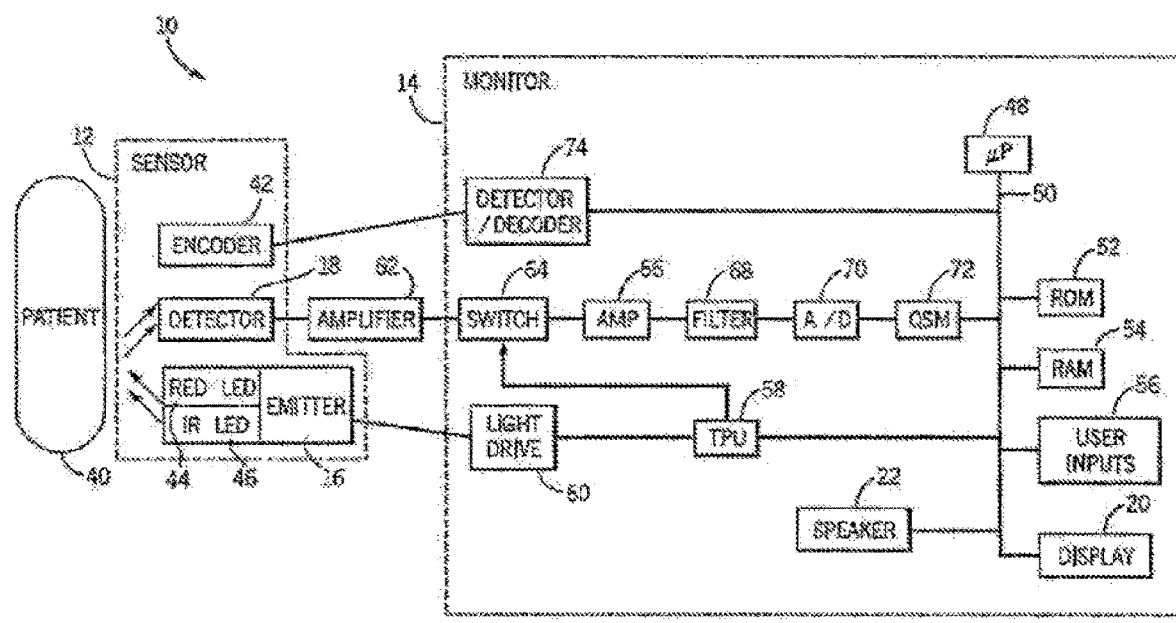
FIG. 2 depicts a block diagram of a traditional pulse oximetry system known in the art field, according to at least some embodiments disclosed herein.

FIG. 2 is a block diagram of the traditional pulse oximetry system 10 of FIG. 1 known in the art field and coupled to a patient 40 in accordance with present embodiments. Specifically, the sensor 12 includes the emitter 16, the detector 18, and an encoder 42. The emitter 16 is configured to emit at least two wavelengths of light, e.g., RED and IR, into the patient's tissue 40. As such, the emitter 16 may include a RED light source (such as a RED LED 44) and an IR light source (such as an IR LED 46) for emitting light into the patient's tissue 40 at the wavelengths used to calculate the patient's physiological parameters. In some examples, the wavelength of the RED LED 44 may be between about 600 nm and about 700 nm and the wavelength of the IR LED 46 may be between about 800 nm and about 1000 nm. It should be appreciated that these ranges are provided for illustrative purposes only. Moreover, it should be appreciated that the quantity of the LED's is not limited to two and other quantities are contemplated herein. Alternative light sources may be used in other embodiments. For example, a single wide-spectrum light source may be used and the detector 18 may be configured to detect light only at certain wavelengths.

It should be understood that, as used herein the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet or X-ray spectra, and that any suitable wavelength of light may be appropriate for use with the present techniques.

In an embodiment, the detector 18 may be configured to detect the intensity of light at the RED and IR wavelengths. In operation, the light enters the detector 18 after passing through the patient's tissue 40. The detector 18 converts the intensity of the received light into an electrical signal. The light intensity is directly related to the absorbance and/or reflectance of light in the patients' tissue 40. As such, when more light at a certain wavelength is absorbed or reflected, less light of that wavelength is received from the tissue by the detector 18. After converting the received light to an electrical signal, the detector 18 sends the signal to the monitor 14, where physiological parameters may be calculated based on the absorption of the RED and IR wavelengths in the patient's tissue 40.

The encoder 42 may contain information about the sensor 12, such as an identification of what type of sensor it is (e.g., whether the sensor is intended for placement on a forehead or the finger of the user) and the wavelengths of light emitted by the emitter 16. This information may be used by the monitor 14 to select appropriate algorithms, lookup tables and/or calibration coefficients stored in the monitor 14 for calculating the patient's physiological parameters.

In addition, the encoder 42 may contain information specific to the patient 40. Such information may include: the patient's age, the patient's gender, the patient's weight, and/or the patient's diagnosis, among other information. This information may allow the monitor 14 to determine patient-specific threshold ranges in which the patient's physiological parameter measurements should fall and to enable or disable additional physiological parameter algorithms. The encoder 42 may, for instance, be a coded resistor that stores values corresponding to the type of the sensor 12, the wavelengths of light emitted by the emitter 16, and/or the patient's characteristics. These coded values may be communicated to the monitor 14, which determines how to calculate the patient's physiological parameters and alarm threshold ranges.

In another embodiment, the encoder 42 may include a memory that may store information, which is then communicated to the monitor 14. Such information may include: the type of the sensor 12, the wavelengths of light emitted by the emitter 16, the proper calibration coefficients and/or algorithms to be used for calculating the patient's physiological parameters and/or alarm threshold values, the patient characteristics to be used for calculating the alarm threshold values, and the patient-specific threshold values to be used for monitoring the physiological parameters.

Signals from the detector 18 and the encoder 42 may be transmitted to the monitor 14. As shown in FIG. 2, the monitor 14 includes a general-purpose microprocessor 48 connected to an internal bus 50. The microprocessor 48 is adapted to execute software, which may include an operating system and one or more applications (such as a voice activation component 76 of FIG. 3), as part of performing the functions described herein. A read-only memory (ROM) 52, a random access memory (RAM) 54, user inputs 56, the display 20, and the speaker 22 are also connected to the interface bus 50.

The RAM 54 and ROM 52 are portrayed for illustrative purposes only. Any computer-readable media may be used in the system for data storage. Computer-readable media are capable of storing information that can be interpreted by the microprocessor 48. This information may be data or may take the form of computer-executable instructions, such as software applications, that cause the microprocessor to perform certain functions and/or computer-implemented methods. Depending on the embodiment, such computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

As shown in FIG. 2, a time processing unit (TPU) 58 provides timing control signals to a light drive circuitry 60, which controls when the emitter 16 is illuminated and multiplexed timing for the RED LED 44 and the IR LED 46. The TPU 58 also controls the gating-in of signals from detector 18 through an amplifier 62 and a switching circuit 64, as shown in FIG. 2. These signals are sampled at the proper time, depending upon which light source is illuminated. The received signal from the detector 18 may be passed through an amplifier 66, a low pass filter 68, and an analog-to-digital (A/D) converter 70. The digital data may then be stored in a queued serial module (QSM) 72 (or buffer) for later downloading to the RAM 54 as the QSM 72 fills up. In one embodiment, there may be multiple separate parallel paths having the amplifier 66, the filter 68, and the AM converter 70 for multiple light wavelengths or spectra received.

The microprocessor 48 may determine the patient's physiological parameters, such as SpO$_2$ reading and the pulse rate, using various algorithms and/or look-up tables based on the value of the received signals corresponding to the light received by the detector 18. Signals corresponding to information about the patient 40, and particularly about the intensity of light emanating from a patient's tissue over time, may be transmitted from the encoder 42 to a decoder 74. These signals may include, for example, encoded information relating to patient characteristics. The decoder 74 may translate these signals to enable the microprocessor to determine the thresholds based on algorithms or look-up tables stored in the ROM 52.

The encoder 42 may also contain the patient-specific alarm thresholds if the alarm values are determined on a workstation separate from the monitor 14. The user inputs 56 may also be used to enter information about the patient, such the patient's age, the patient's gender, the patient's height, the patient's weight, medications the patient is taking, treatments the patient is engaging in, and/or the patient's diagnosis, among others. In some examples, the display 20 may exhibit a list of values that may generally apply to the patient, such as, for example, age ranges or medication families, which the user may select using the user inputs 56. The microprocessor 48 may then determine the proper thresholds using the user input data and algorithms stored in the ROM 52. The patient-specific thresholds may be stored on the RAM 54 for comparison to measured physiological characteristics. The ROM 52 and the RAM 54 may also store information for use in selection of a power consumption mode based on the data generated by the sensor 12 and/or monitor 14.

Figure 3:
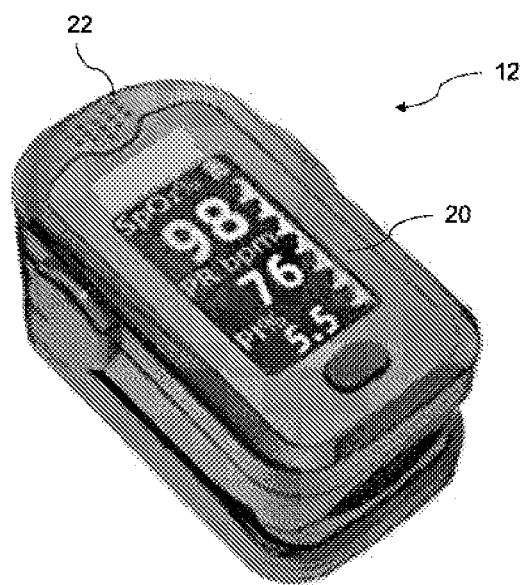
FIG. 3 depicts a schematic diagram of a pulse oximetry system of the present invention, according to at least some embodiments disclosed herein.

FIG. 3 depicts a schematic diagram of the pulse oximetry system 10 of the present invention. As shown in FIG. 3, and similar to the pulse oximetry system 10 of FIG. 1 and FIG. 2, the pulse oximetry system 10 of FIG. 3 includes the sensor 12, the display 20, and/or the speaker 22, among other components not explicitly listed herein. Differing from the pulse oximetry system 10 of FIG. 1 and FIG. 2, the pulse oximetry system 10 of FIG. 3 may wirelessly interact with a mobile device 80 vi a network 92, such as the Internet, as depicted in FIG. 4.

Figure 4:
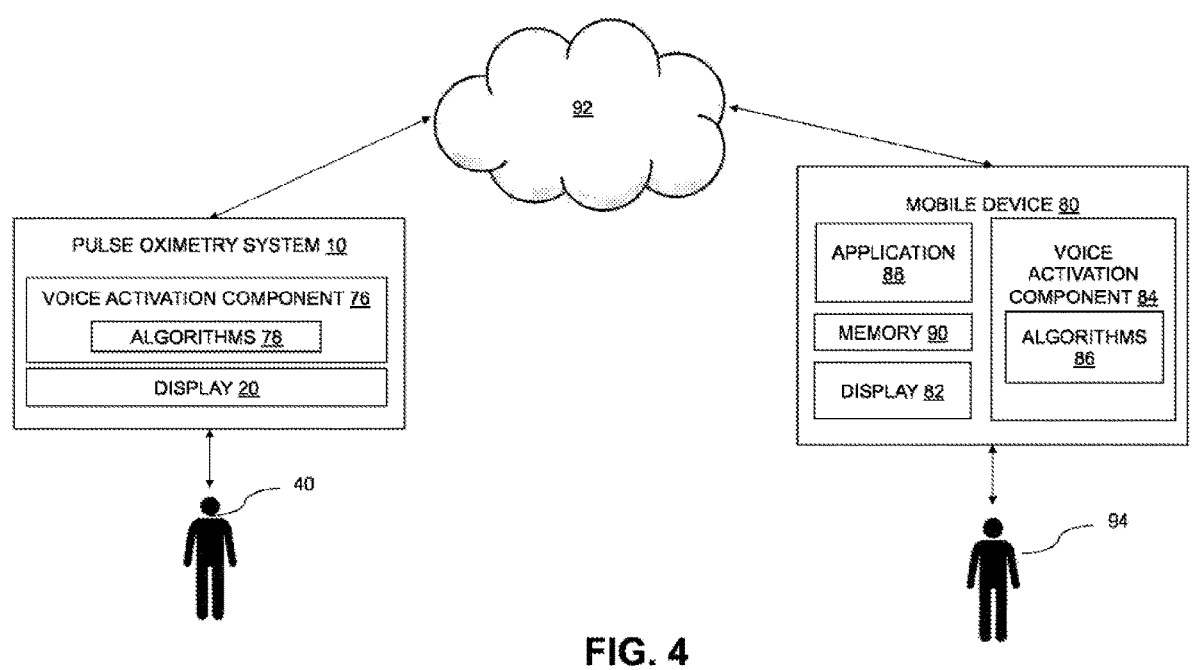
FIG. 4 depicts a schematic diagram of a pulse oximetry system configured to interact with a mobile device over a network, according to at least some embodiments disclosed herein.

A system is depicted in FIG. 4. The system of FIG. 4 includes the pulse oximetry system associated with a first user 40, the mobile device 80 associated with a second user 94, and the network 92, such as the Internet. In some examples, each of the first user 40 and the second user 94 may be a patient, a doctor, or a healthcare worker.

As shown in FIG. 4, the pulse oximetry system 10 may communicate directly or indirectly with mobile device 80 via the network 92. In examples, the pulse oximetry system 10 may comprise a cellular modem (not shown) to communicate and/or transmit measurement results to the mobile device 80 or another computing device, such as a smartphone, a laptop computer, a tablet, or another suitable computing device. It should be appreciated that, as described herein, the cellular modem is a device that adds cellular connectivity to laptops, desktop computers, tablets, and other similar devices. Furthermore, it should be appreciated that the cellular modem (not shown) replaces the existing BLE module in the Bluetooth devices described herein.

In examples, the cellular modem may be embedded within the pulse oximetry system 10 or may be a standalone device that is connected to the pulse oximetry system 10 through various means, including, but not limited to, a USB connection. Examples of cellular modems include, but are not limited to, AT&T Momentum, Verizon 551 L, USB cellular modems and motherboard mounted cellular chipsets manufactured by Novatel Wireless, Sierra Wireless, Huawei, and the like. In other examples, the cellular modem may operate by switching between cellular and satellite communications.

Furthermore, the cellular modem may be configured to automatically connect to a slower network when the faster network is not available. The cellular modem may also monitor the reliability of all available connections. The reliability of a network can be determined from information collected by the cellular modem, which includes, but is not limited to, signal strength, quality, availability, packet loss, retransmits, packet latency, throughput speed, and other cell tower signaling quality factors. The cellular modem may then compare this information in various forms to a reliability threshold in order to determine whether or not to maintain or terminate a connection to a cellular network. The reliability threshold is often automatically set by the cellular carrier, or may be manually set by the user of the pulse oximetry system 10.

Further, it should be appreciated that the cellular modem is also configured to establish a connection with cellular networks in which the cellular modem is located. The cellular modem is configured to monitor and detect all cellular networks as the cellular modem moves from one network coverage area to another network coverage area via a vehicle in which it is contained. The cellular modem can detect when a connection to a particular network is made, whether it is a 3G, 4G, or 5G network, as well as which cellular network provider (e.g., Verizon, T-Mobile, etc.) it has connected to.

In an example, and as depicted in FIG. 4, an application 88 is executed on the mobile device 80. It should be appreciated that in other examples, the application 88 may be an engine, a software program, a service, or a software platform executable on the mobile device 80. The second user 94 may input information into the application 88, such as blood oxygen saturation readings, pulse rate readings, age, weight, medications that the user is currently taking, treatments the user is currently undergoing, etc. The application 88 also allows the second user 94 to share data and progress with another user.

The memory of the pulse oximetry system 10 (e.g., the ROM 52 and/or the RAM 54) and the memory 90 of the mobile device 80 store user data and information. The elements stored in memory of the pulse oximetry system 10 (e.g., the ROM 52 and/or the RAM 54) and the memory 90 of the mobile device 80 may also be synchronized and stored remotely in a cloud-based storage. It should be appreciated that numerous profiles (such as a first user profile A 96 associated with the first user 40 and a second user profile B 98 associated with the second user 94) may be stored in the memory of the pulse oximetry system 10 (e.g., the ROM 52 and/or the RAM 54) and the memory 90 of the mobile device 80 and the quantity of the profiles is not limited to two.

Figure 5:
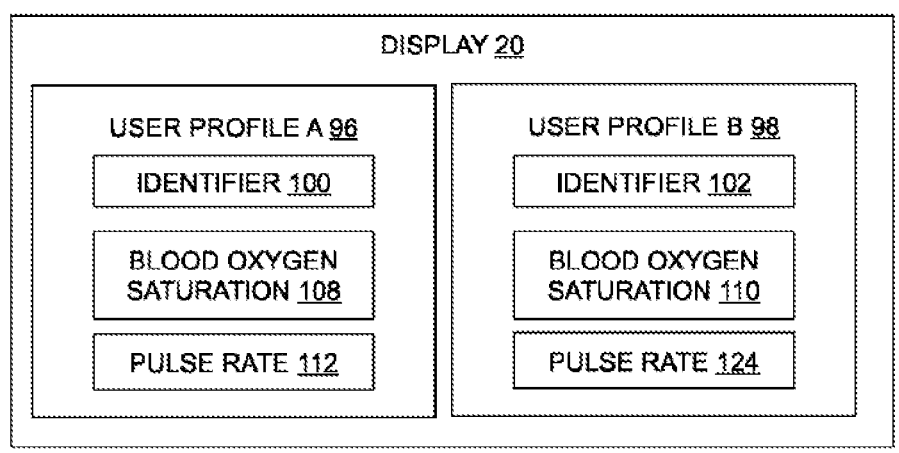
FIG. 5-FIG. 7 depict block diagrams of a display of a pulse oximetry system, according to at least some embodiments disclosed herein.

As shown in FIG. 5, each of the user profiles (e.g., the first user profile A 96 and the second user profile B 98) may include a unique identifier associated with the user of the profile. For example, a first identifier 100 may be associated with the first user and may be stored in the first user profile A 96 and a second identifier 102 may be associated with the second user and may be stored in the second user profile B 98. For illustrative purposes only, the unique identifier may be a numerical code, an alphanumeric code, a username, etc. Each of the first user profile A 96 and the second user profile B 98 may also include the blood oxygen saturation readings and the pulse rate readings. More specifically, the first user profile A 96 may include the blood oxygen saturation reading 108 and the pulse rate reading 112 and the second user profile B 98 may include the blood oxygen saturation reading 110 and the pulse rate reading 124. It should be appreciated that the blood oxygen saturation readings and the pulse rate readings may be updated with a new entry every time a particular individual uses the pulse oximetry system 10.

Figure 6:
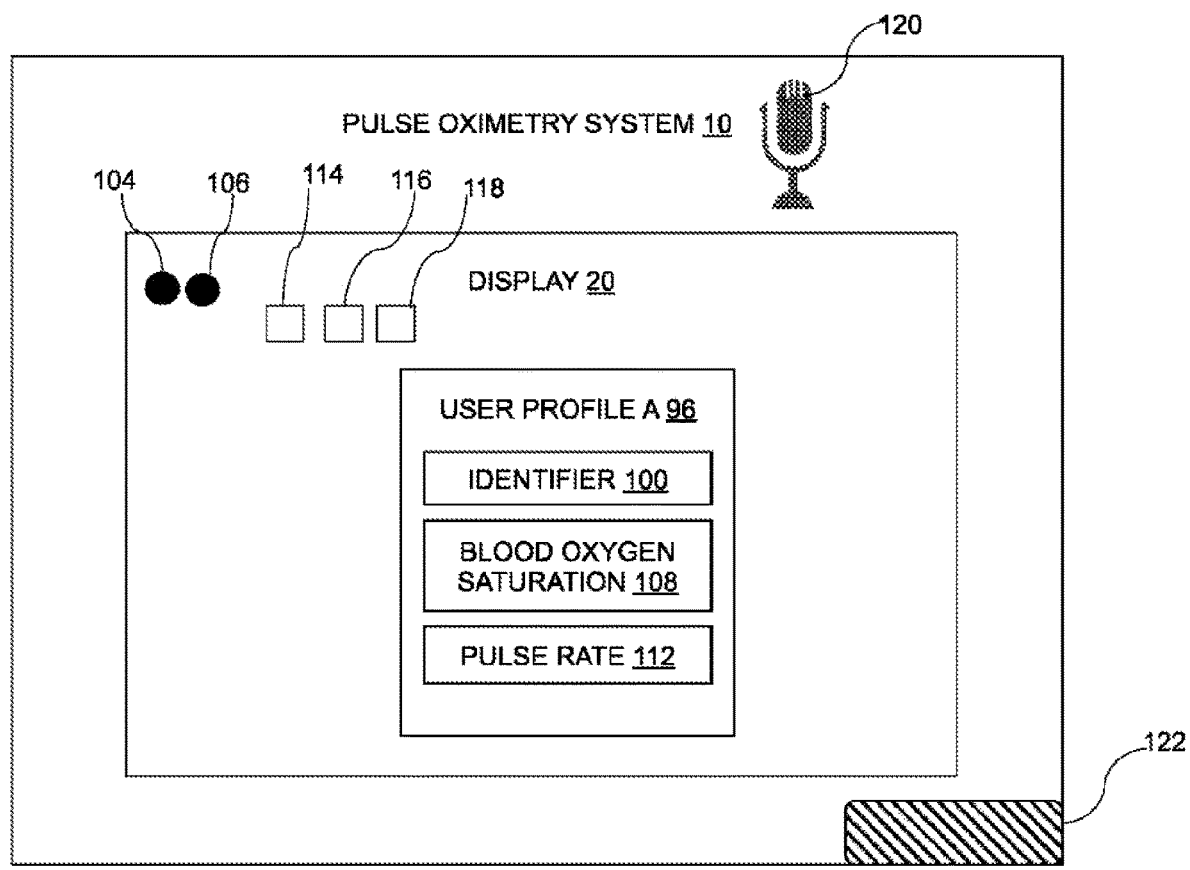
Figure 7:
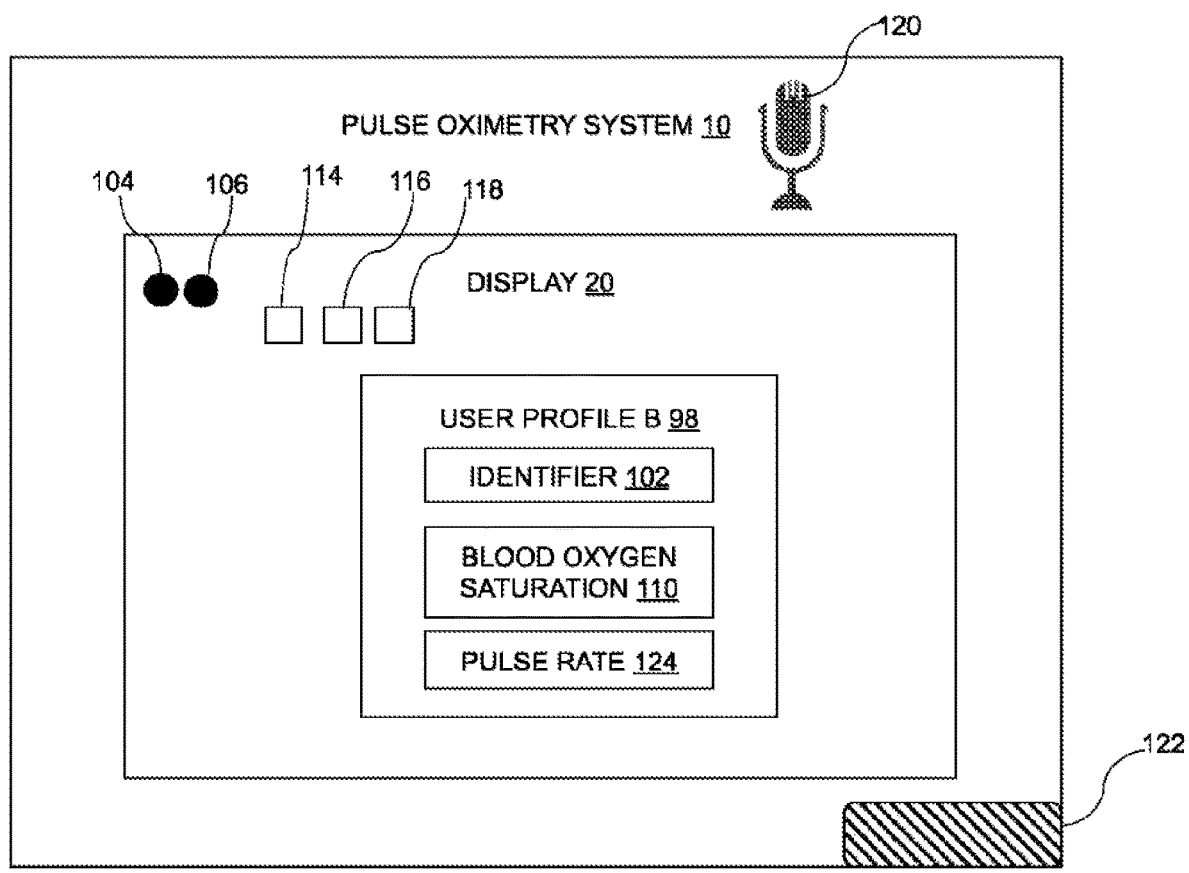

An interactive display 20 of the pulse oximetry system 10 is depicted in FIG. 5, FIG. 6, and FIG. 7. It should be appreciated that the interactive display 20 may have additional or fewer features from the ones described and depicted herein. In one embodiment, the interactive display is touch-enabled.

The interactive display 20 allows the first user 40, the second user 94, or another user to view data described herein in numerous ways. In an example, the interactive display 20 provides a screen that changes based on user selection of a button, such as a first button 114, a second button 116, and/or a third button 118. Upon user selection of the first button 114, as shown in FIG. 6, the interactive display 20 displays the user profile associated with the given user. For example, the interactive display 20 displays the first user profile A 96 of the first user 40, which includes the first identifier 100 associated with the first user 40, the current blood oxygen saturation reading 108 of the first user 40, and the current pulse rate reading 112 of the first user 40. Other raw scale data could also be displayed.

In another example, the pulse oximetry system 10 may include a switch component 122 (of FIG. 5, FIG. 6, and FIG. 7). The switch component 122 may receive an action, such as a touch or tap action, indicating that a given user wishes to switch information displayed via the interactive display 20 to another profile or to other information.

The processor of the pulse oximetry system 10 may include a voice activation component 76. Further, the pulse oximetry system 10 may also include a microphone 120. The voice activation component 76 may include one or more algorithms 78. In an example, the first user 40 provides an audio input to the microphone 120 (of FIG. 6 and FIG. 7) of the pulse oximetry system 10. The microphone 120 may receive the login credentials from the first user 40 via the audio input. Next, the one or more algorithms 78 of the voice activation component 76 of the pulse oximetry system 10 analyze the login credentials to determine whether the login credentials corresponds to login credentials associated with a user profile stored in the memory (e.g., the ROM 52 and/or the RAM 54) of the pulse oximetry system 10 (such as a first user profile A 96 associated with the first user or a second user profile B 98 associated with the second user of FIG. 5). In response to a determination that the login credentials of the audio input correspond to the login credentials associated with the first user profile A 96, the one or more algorithms 78 of the voice activation component 76 confirm the identity of the user as the first user. In another example, the second user 94 may provide the login credentials via a physical input to the mobile device 80.

In other examples, voice activation may be used to prompt the pulse oximetry system 10 to perform an action, such as display the first user profile A 96 associated with the first user 40 or display different items or information associated with the first user profile A 96 on the interactive display 20. Voice activation may also be used to perform actions on the mobile device As explained, the pulse oximetry system 10 comprises the voice activation component 76 (or module) and the mobile device 80 comprises the voice activation component 84 (or module). The voice activation component 76 may be used to control actions of the pulse oximetry system and the voice activation component 84 may be used to control actions of the mobile device respectively.

Further, the voice activation component 76 of the pulse oximetry system 10 comprises the one or more algorithms 78 and the voice activation component 84 of the mobile device 80 comprises the one or more algorithms 86. In an example, when the microphone 120 of the pulse oximetry system 10 receives an audio input from the user, the one or more algorithms 78 of the voice activation component 76 analyze the audio input to determine whether the audio input corresponds to a command recognizable by the voice activation component 76. Such recognizable commands are stored in the memory of the pulse oximetry system 10. In other examples, the recognizable commands are stored in a data store (not shown). If the voice input corresponds to a recognizable command, the pulse oximetry system 10 may process and execute the command.

In some examples, a microphone (not shown) of the mobile device 80 receives the audio input from the user. In response, the one or more algorithms 86 of the voice activation component 84 of the mobile device 80 analyze the audio input to determine whether the audio input corresponds to a command recognizable by the voice activation component 84. Such recognizable commands are stored in the memory or a data store (not shown) of the mobile device 80. If the voice input corresponds to a recognizable command, the mobile device 80 may process and execute the command.

The command can include any of a number of functions or operations supported by pulse oximetry system 10 or the mobile device 80. It should be appreciated that the recognizable commands may include: turn on the device, turn off the device, awake the device from a sleep mode, put the device into the sleep mode, display the first user profile A 96, and/or display the second user profile B 98, etc. It should be appreciated that the pulse oximetry system 10 or the mobile device 80 may utilize user input devices to replace or supplement voice commands.

It should be appreciated that in some implementations, the mobile device 80 may comprise an intelligent personal assistant and knowledge manager, such as Siri, and/or a virtual assistant artificial intelligence (AI) technology developed by Amazon, Amazon Alexa. In this example, the mobile device 80 may first receive an action on a physical button, icon, or display of the mobile device 80. In response, the mobile device 80 may launch Siri or Amazon Alexa. Then, the user may provide audio input, via the microphone, to the mobile device 80. Siri or Amazon Alexa may process the audio input and provide an audio response via a speaker of the mobile device 80 or a visual response via the display 82 of the mobile device 80. In some examples, the audio or visual response may be transmitted to the pulse oximetry system 10 for storage and/or display to the user.

As described herein, "Siri" is a software application, and more particularly, an intelligent personal assistant and knowledge manager. Siri is part of Apple Inc.'s iOS, iPadOS, watchOS, macOS, and tvOS operating systems. The assistant uses voice queries, gesture based control, focus-tracking and a natural-language user interface to answer questions, make recommendations, and perform actions by delegating requests to a set of Internet services. The software adapts to users' individual language usages, searches, and preferences, with continuing use. Returned results are individualized. Siri supports a wide range of user commands, including performing phone actions, checking basic information, scheduling events and reminders, handling device settings, searching the Internet, navigating areas, finding information on entertainment, and is able to engage with iOS-integrated apps.

As described herein, "Amazon Alexa" or "Alexa" is a virtual assistant AI technology developed by Amazon. Alexa is capable of voice interaction, music playback, making to-do lists, setting alarms, streaming podcasts, playing audiobooks, and providing weather, traffic, sports, and other real-time information, such as news. Alexa can also control several smart devices using itself as a home automation system. Users are able to extend the Alexa capabilities by installing "skills" (additional functionality developed by third-party vendors, in other settings more commonly called apps such as weather programs and audio features).

Moreover, the interactive display 20 of the pulse oximetry system 10, as shown in FIG. 5, FIG. 6, and FIG. 7, may also include one or more indicators 104, 106 to remind an individual to utilize the pulse oximetry system 10 to take readings. Further, in examples, the one or more indicators 104, 106 may be one or more light-emitting diodes (LEDs) of various colors. The one or more indicators 104, 106 may be used in a number of ways.

The one or more indicators 104, 106 may flash, strobe, or change color. In another example, the first user 40 associated with the first user profile A 96 may be assigned a color of green and the second user 94 associated with the second user profile B 98 may be assigned a color of red. Such colors may be stored in the respective user profile. If the first user 40, for example, fails to use the pulse oximetry system 10 for more than a specified time period (e.g., a week), the one or more indicators 104, 106 may flash the color green at a low duty-cycle. In the same example, if the second user 94 fails to use the pulse oximetry system 10 for more than a specified time period, the one or more indicators 158A, 158B may flash the color red at a low duty-cycle. The duty-cycle may increase successively as more time elapses between consecutive weigh-ins by the scale user.

In another example, the mobile device 80 may send a user-identifying signal to the pulse oximetry system 10 when the mobile device 80 is in proximity to pulse oximetry system 10. In an alternate embodiment, the one or more indicators 104, 106 may also include audio indicators. In this embodiment, the one or more indicators 104, 106 illuminate or sound (e.g., a tone, a beep, an alarm, etc.) when mobile device 110 is in proximity to the pulse oximetry system 10.

Furthermore, as depicted in at least FIG. 5, FIG. 6, and FIG. 7, the one or more indicators 104, 106 are located on a same surface as the display 20. In another example, the one or more indicators 104, 106 may be located on a different surface of the pulse oximetry system 10.

If a predetermined amount of time has passed (e.g., a week), the color of the one or more indicators 104, 106 may pulse to indicate that it has been longer than the predetermined amount of time since the given user has taken a measurement using the pulse oximetry system 10. The pulse could then turn into an on-off flashing pattern after a longer period of time has elapsed (e.g., two weeks).

In an embodiment, the system described herein may also include a key fob (not shown). The key fob may contain wireless signal capabilities. The key fob is configured to transmit a signal to the pulse oximetry system 10 when the key fob is within a proximity to the pulse oximetry system 10. In response to receiving the signal from the key fob, the one or more indicators 104, 106 may increase light intensity for the user identified by the key fob. For example, once the key fob transmits the signal to the pulse oximetry system 10 when the key fob is within the proximity to the pulse oximetry system 10, the one or more indicators 104, 106 may increase light intensity for the color green for the user (e.g., the first user 40) identified by the key fob.

Another embodiment of the invention provides a method that performs the process steps on a subscription, advertising, and/or fee basis. That is, a service provider can offer to assist in the method steps described herein. In this case, the service provider can create, maintain, and/or support, etc. a computer infrastructure that performs the process steps for one or more customers. In return, the service provider can receive payment from the customer(s) under a subscription and/or fee agreement, and/or the service provider can receive payment from the sale of advertising content to one or more third parties.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A system comprising:
a network, wherein the network is one of a 4G or 5G cellular network;
a pulse oximeter configured to communicate, via the network, with a mobile device, the pulse oximeter comprising:
a sensor component comprising:
a first side disposed opposite a second side; and
a receiving portion configured to receive a finger of an individual therein,
wherein the first side comprises an emitter component configured to emit light at one or more wavelengths into tissue of the finger of the individual, and
wherein the second side comprises a detector component configured to detect the light originating from the emitter component that emanates from the tissue of the finger of the individual after passing through the tissue;
an engine configured to calculate physiological parameters for the individual based on data received from the sensor component, the engine comprising:
a memory; and
a processor connected to the memory;

a speaker, wherein the speaker includes audio emitting capabilities;
a button configured to enable a user to control a function of the device; and
a key fob that contains wireless signal capabilities,
wherein the key fob is configured to transmit a signal to the processor when the key fob is in proximity of the pulse oximeter, and
wherein the processor is configured to:
receive the signal from the key fob;
select, based on the signal, a user profile from the memory corresponding to an owner of the key fob; and
store a blood oxygen saturation reading or a pulse rate reading of the individual in the user profile when the owner of the key fob is a corresponding user.

2. The system of claim 1, wherein the memory stores a plurality of user profiles, wherein each of the plurality of user profiles is associated with a corresponding user.

3. The system of claim 2, wherein the processor is configured to:
receive a signal from the mobile device;
select a user profile from the memory corresponding to an owner of the mobile device; and
store a blood oxygen saturation reading and/or a pulse rate reading of the individual in one of the plurality of user profiles when the owner of the mobile device is one of the corresponding users.

4. The system of claim 1, wherein the pulse oximeter further comprises one or more grips,
wherein the one or more grips are configured to enable the user to more effectively hold and change positions of the first and second sides relative to one another so that a user's finger easily enters the receiving portion of the sensor, and
wherein the one or more grips comprise one or more shapes raised relative to the sensor.

5. The system of claim 1, wherein the physiological parameters for the individual are selected from the group consisting of: a blood oxygen saturation reading and a pulse rate reading.

6. The system of claim 1, wherein the pulse oximeter further comprises:
a display configured to display data to the individual, including blood oxygen level, pulse rate waveform, pulse rate value, pulse column, battery strength, and network connectivity status.

7. The system of claim 1, wherein the pulse oximeter further comprises:
a data input device configured to receive a physical input from the individual.

8. The system of claim 1, wherein the button is further configured to enable the user to power the device on and off.

9. The system of claim 1, wherein the speaker is configured to emit a sound when at least one of the users is in proximity to the pulse oximeter, and the speaker is configured to emit a sound when the engine determines that the physiological parameters of at least one of the users are outside a predetermined range.

10. The system of claim 1,
wherein the mobile device comprises an application executed on the mobile device, and
wherein the application is configured to track blood oxygen saturation readings and pulse rate readings for one or more users.

11. The system of claim 1, wherein the mobile device is configured to send a signal via the network to the processor when the mobile device is in proximity to the pulse oximeter.

12. The system of claim 1, wherein the processor further comprises a voice activated component, and wherein the system further includes:
a microphone configured to receive an audio input from the individual,
wherein the voice activation component comprises one or more algorithms, the one or more algorithms being configured to:
analyze the audio input received via the microphone;
compare the audio input to commands stored in the memory;
determine that the audio corresponds to a command of the commands stored in the memory based on a comparison; and
process and execute the command.

13. A pulse oximeter comprising:
a sensor component comprising:
a first side disposed opposite a second side; and
a receiving portion configured to receive a finger of an individual therein,
wherein the first side comprises an emitter component configured to emit light at one or more wavelengths into a tissue of the finger of the individual, and
wherein the second side comprises a detector component configured to detect the light originating from the emitter component that emanates from the tissue of the finger of the individual after passing through the tissue; and
an engine configured to calculate physiological parameters for the individual based on data received from the sensor component, the engine comprising:
a memory storing one or more user profiles associated with one or more users;
a processor connected to the memory; and
a display, the display configured to display data to the individual, including blood oxygen level, pulse rate waveform, pulse rate value, pulse column, battery strength, and network connectivity status,
wherein the display includes one or more indicators including one or more light-emitting diodes (LEDs), and
wherein the one or more indicators comprise an audio functionality such that the one or more indicators project or flash light and/or emanate a sound when the individual is within a proximity of the pulse oximeter; and a key fob that contains wireless signal capabilities,
wherein the key fob is configured to transmit a signal to the processor when the key fob is in proximity of the pulse oximeter, and
wherein the processor is configured to:
receive the signal from the key fob;
select, based on the signal, a user profile from the memory corresponding to an owner of the key fob; and
store a blood oxygen saturation reading or a pulse rate reading of the individual in the user profile when the owner of the key fob is a corresponding user.

14. The pulse oximeter of claim 13, wherein the physiological parameters for the individual are selected from the group consisting of: a blood oxygen saturation reading and a pulse rate reading.

15. The pulse oximeter of claim 13, wherein the pulse oximeter is configured to communicate with a mobile device via a network.

16. The pulse oximeter of claim 13,
wherein the one or more user profiles comprises blood oxygen saturation readings for a user, pulse rate readings for a user, and a unique identifier for a user.

17. The pulse oximeter of claim 13,
wherein the one or more users are each associated with a color of light configured to be emitted from the one or more indicators, and
wherein the color of light differs with each of the one or more users.

18. The pulse oximeter of claim 17,
wherein the color of light is stored in the one or more user profiles, and wherein the one or more indicators are configured to project the color of light when one of the one or more users fail to use the pulse oximeter for a predetermined period of time.

\* \* \* \* \*